Figure 1:
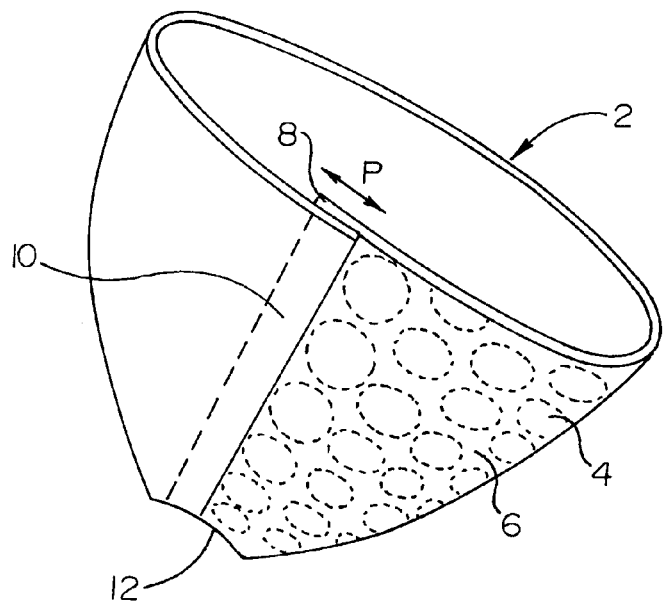

United States Patent [19]
Gronholz

[11] Patent Number: 6,149,619
[45] Date of Patent: Nov. 21, 2000

[54] BRA INSERT

[75] Inventor: Claus Gronholz, Norderstedt, Germany

[73] Assignee: Umwelt-Technics-Nord GmbH, Norderstedt, Germany

[21] Appl. No.: 08/981,936
[22] PCT Filed: Jun. 26, 1996
[86] PCT No.: PCT/EP96/02820
 § 371 Date: Mar. 17, 1998
 § 102(e) Date: Mar. 17, 1998
[87] PCT Pub. No.: WO97/01994
 PCT Pub. Date: Jan. 23, 1997

[30]  Foreign Application Priority Data

Jun. 30, 1995 [DE] Germany .......................... 195 23 920

[51] Int. Cl.[7] .................................................. A61N 1/30
[52] U.S. Cl. ............................ 604/20; 424/449; 450/2; 602/48; 604/304

[58] Field of Search .............................. 604/20, 290, 304; 424/447, 449; 602/48; 2/104, 114; 450/37, 38

[56]  References Cited

U.S. PATENT DOCUMENTS

| | | |
|---|---|---|
| 1,862,122 | 6/1932 | Schrader . |
| 2,764,976 | 10/1956 | Skiles . |
| 4,619,252 | 10/1986 | Ibbott . |
| 4,921,704 | 5/1990 | Fabo . |
| 5,123,900 | 6/1992 | Wick . |
| 5,843,018 | 12/1998 | Shesol et al. . |

*Primary Examiner*—Mark Bockelman
*Attorney, Agent, or Firm*—Vidas, Arrett & Steinkraus, P.A.

[57]  ABSTRACT

An insert for a bra, wherein the insert adaptable to the inner shape of the cup comprises at least one zone storing an active ingredient and delivering to the skin, and at least one breathing compensation zone, wherein the zones selectively deliver active ingredients only or act in a compensating manner, or carry out both functions simultaneously.

31 Claims, 2 Drawing Sheets

BRA INSERT

The invention relates to an insert adapting to the cup shape for a bra.

For the care of the female breast there are active ingredient preparations, for example creams or fluids which are applied to the skin of the breasts in order to act over a longer period of time. With the direct application on the skin a metering of the active ingredient preparations is possible only with difficulty or is very time consuming, for example by repeated application of small amounts. A uniform metering over a longer period of time may be achieved in this manner only to a certain extent.

Inserts for bras are known which serve various purposes. There are for example breastfeeding inserts (see G 81 19 845.0, DE 32 06 371 A1 or G 8315 729.9) and shape-inserts (see DE 31 20 875 C2).

It is the object of the invention to provide an insert for a bra, via which active ingredients, for the care of the female breast or for its therapeutic treatment in a comfortable manner and with a constant metering, can be brought into contact with the skin.

The object is achieved in that the insert adaptable to the inner shape of the cup comprises a zone which stores the active ingredients and delivers to the skin, and at least one breathing compensation zone.

Advantages of the insert are that the active ingredient zones serve as reservoirs for the active ingredient preparations and simultaneously deliver one or more active ingredients to the skin, wherein the delivery quantity is co-determined by the nature of the active ingredient zones, as is described below. Furthermore the compensation zone of the insert serves as a breathing region, in particular for avoiding the formation of sweat. It is however also possible without further ado that the active ingredient zone is at the same time a breathing region.

The insert advantageously covers essentially the whole inner surface of the cup. In order to maximise the effect of the insert, preferably the size of the active ingredient and compensation zones is selected such that their total surface corresponds essentially to the total surface of the insert. In an advantageous embodiment of the invention a multitude of active ingredient zones and a multitude of compensation zones are provided which are arranged alternately. With this the zones of one type may be separated from one another, arranged in an island manner within the zone of the other type. It is favourable when the zones run strip-shaped in the circumferential direction or in the longitudinal direction. If the zones are arranged in an island manner within another zone, a round circumferential shape of the zones arranged in an island-like manner may be advantageous.

According to a further advantageous embodiment the insert comprise several layers, of which one contains the active ingredient zones and the compensation zones. On this layer a further layer may be connected which lies further outside, which is breathing and is fluid permeable at least in the regions bordering the active ingredient zones. In this way it is achieved that the active ingredient preparation which as a rule is fluid or viscous or the carrier substance in which the active ingredients are contained, these being contained in the active ingredient zones, cannot exit into the bra. Towards the inside a further layer may be connected to the storing layer, this further layer able to serve for the transmission of the active ingredient and also for transmission of the body substances to be taken up by the compensation zones. On application of such a transmission layer, this comes into direct contact with the skin in place of the storing layer. Also the transmission zone may comprise various zones which are congruent with the active ingredient zones or the compensation zones and comprise various transmission properties corresponding to these. So that an active ingredient preparation, already added on manufacture of the insert, may not exit the insert already before its use or may not lose its effectiveness, as an innermost layer a removable protective film which is airtight may be provided. Alternatively the whole insert after its manufacture may be sealed by an encompassing foil. It may also be provided that the active ingredient zones are not provided already on manufacture of the insert with an active ingredient preparation, but that the active ingredient zones are provided with an active ingredient preparation by the user, for example by introducing drop by drop. Furthermore it may also be provided that the user after use of the insert, refills active ingredient preparations into the active ingredient zones.

In particular when the total surfaces of the active ingredient zones and the compensation zones are to be a maximum, the various zones may directly border onto one another. Preferably then the bordering surfaces are so created between the zones that they have a limited permeability. For the active ingredient preparation and the carrier substance there should be practically no permeabilty. If the active ingredient zones or the compensation zones do not directly border one another, between these zones there may lie further zones which are "neutral". Preferably these "neutral" zones, similar to the bordering areas between directly bordering active ingredient and compensation zones, have practically no permeability for the active ingredient preparation and the carrier fluid.

So that the insert may be well adapted to the shape of a bra cup, the insert is preferably manufactured from a flexible material. On the inner side the insert may act thermoplastically in order to provide an inner contact given the skin surface temperature. The insert may be a flat strip, which is rolled up and closed with a self-adhesing closure. The flat strip may be so formed that it has a conical form on its rolling up. Additionally or alternatively, the material of the flat strip may be so soft that the rolled up flat strip adapts very easily to the cup shape. This flat strip may comprise weakening lines along which part of the flat strip may be removed for its shortening, in order to adapt the size of the insert to the cup. The insert then when it is a rolled-up flat strip as well as when it is manufactured initially in the cup shape, may comprise a separating line in the longitudinal direction, wherein the two lateral regions along the line adjustably overlap for changing the size. An adaptation of the insert to bra cups of various sizes may also be achieved in that the insert comprises recesses in the longitudinal direction which extent from the largest circumferential line so that the wall segments located between these may bend towards the inside without folds forming. Further on the outside the insert may comprise one or more self-adhesing regions which serve the fastening in the bra cup. Preferably this insert may have a dimensional stability of its own so that it comprises a cup shape without being connected to the bra.

An insert which has such a predetermined shape may be used on its own, that is without combination with a bra. This may for example occur for therapeutic purposes.

In the following various embodiments of the active ingredient zones are described which are designed with properties for metering the active ingredients. In particular when the active ingredient comprises a relatively high viscosity, the active ingredient zones may be formed hygroscopically in order for example by way of the uptake of body moisture to gradually thin or let the fluid become more fluid.

A further possibility for the metering of the active ingredient may consist of providing a pressure difference between the active ingredient regions and the skin, by way of which ions or molecules of the active ingredient preparation exert a certain pressure on the skin. By way of varying concentrations of the active ingredient a transport in the direction of the skin can be effected (controlled release). A deposition of certain ions or molecules on the skin may be achieved in that an electrical voltage is applied at least over the thickness of the active ingredient zones, i.e. by way of a foil battery, by which means it is achieved that certain ions or molecules dependent on charge accumulate at one electrode which borders the skin or is insulated by the skin. According to a futher embodiment of the invention the active ingredient zones on the inner side may be limited by a diaphragm-like separating layer, so that the active ingredients may act osmotically on the skin. The applied active ingredient preparation may further be so formed that the active ingredients are located in a carrier substance which liquifies when heated up, or the active ingredients may themselves form a substance which has this property. The heating up is effected by the body temperature. There may also be provided substances which are thixotropic. A further possibility for metering the active ingredients lies in limiting the active ingredient zones at their inner side by a membrane whose permeability to the active ingredient increases on heating. There may also be provided a membrane whose permeability to the active ingredient increases on the effect of force by movement changes of the insert, i.e. with body movements. The active incredients may also be materials lowering the interfacial tension (capillary active) which for example accumulate on the border surfaces between the active ingredient zones and the skin. The active ingredient zones with this embodiment are formed as border surface systems.

Figure 2A:
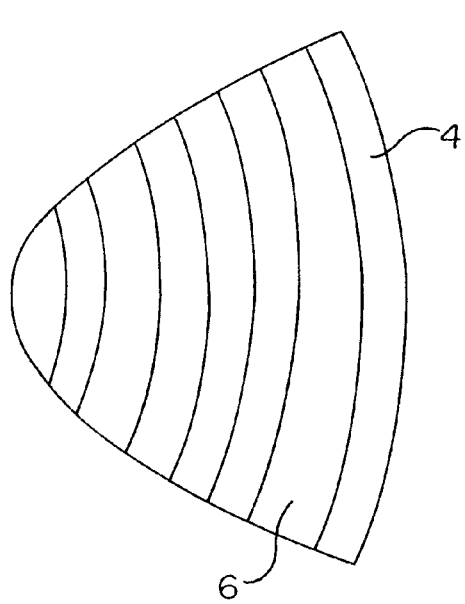
Figure 2B:
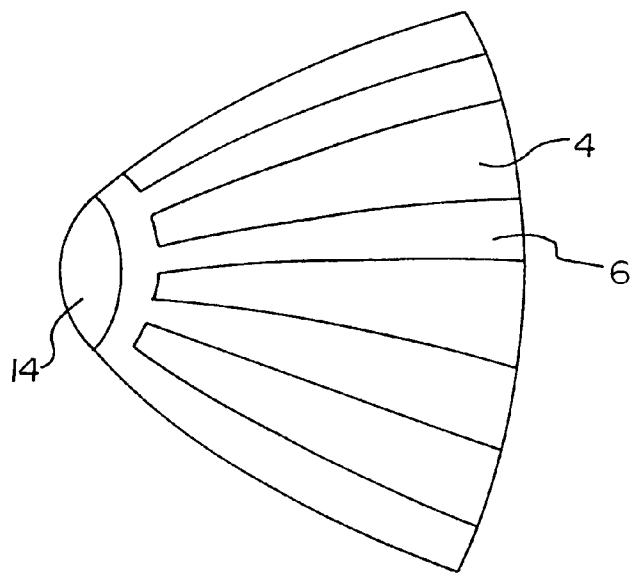
Figure 3:
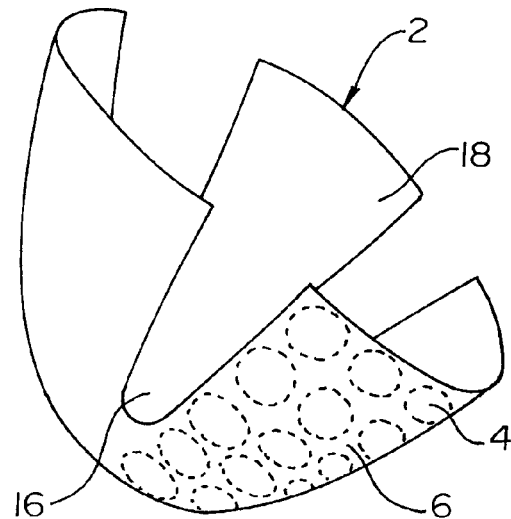
Figure 4:
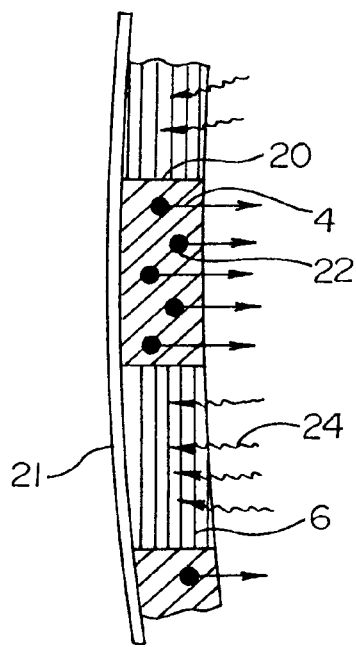
Figure 5:
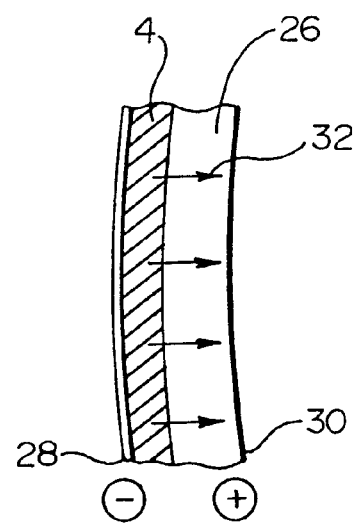

The invention is described in more detail by way of the subsequent drawings. The drawings show:

FIG. 1 a perspective view of an insert adjustable in size;

FIGS. 2a and 2b lateral views of inserts with strip-shaped active ingredient zones and compensation zones;

FIG. 3 a perspective view of an insert with recesses and wall segments for adapting the size of the insert;

FIG. 4 a schematic part section view of an arrangement of active ingredient zones and compensation zones and of a bordering bra material;

FIG. 5 a part section view of an active ingredient zone with a bordering transmission zone and an applied electrical voltage.

In all figures the same parts are indicated with the same reference numerals.

FIG. 1 shows an insert 2 with a multitude of active ingredient zones 4 which have a round circumferential shape. The active ingredient zones are arranged over the whole surface of the insert, but are not shown on the left side of the insert for reasons of clarity. Regions between the active ingredient zones together form a compensation zone 6. The insert comprises in the longitudinal direction a separating line, and two lateral regions 8, 10 along the line which overlap, wherein the thickness of the overlapping as is shown by the double arrow P, is adjustable in order to be able to adapt the size of the insert to the size of the cup. The insert comprises at the front end an opening 12 which serves so that the nipple does not come into contact with the insert.

It is however also possible that the zones 4 may simultaneously be breathing compensation zones.

The FIGS. 2a and 2b show inserts with strip-shaped active ingredient zones 4 and essentially strip-shaped compensation zones 6. With the insert of FIG. 2a the strips 4, 6 are arranged in the circumferential direction, in FIG. 2b on the other hand they are arranged in the longitudinal direction. Both inserts are, in contrast to the insert shown in FIG. 1, closed at the front end. Whilst the insert of FIG. 2a is formed with a compensation zone at the front end, the insert of FIG. 2b at the front end neither comprises a compensation zone nor an active ingredient zone. The front end represents a further zone of a "neutral" zone 14 within a layer containing the active ingredient zones and the compensation zones.

FIG. 3 shows an insert with active ingredient zones 4 and compensation zones 6 which are arranged as with the insert of FIG. 1. For size adaptation of the insert 2 to the size of a cup there are three recesses 16 extending in the longitudinal direction from the border edge, these having a wedge-like and rounded shape tapering towards the front end of the insert. With these recesses the insert is subdivided into three wall segments 18 which are connected to one another via the front end of insert, and which on lateral pressure can bend inwards by which means the circumference of the insert may be reduced without folds forming.

FIG. 4 explains the functioning principle of the active ingredient zones 4 and the compensation zones 6. With the arrangement shown in FIG. 4 of these two zone types, these alternately directly border onto one another. They are separated by border surfaces 20 which are not permeable to the active ingredient preparation present in the active ingredient zone. On a longitudinal side which forms the outer side, the zones rest against a bra material. This material is selected such that the active ingredient particles 22 may only exit through the longitudinal side lying opposite, thus inwardly towards the skin from the active ingredient zones as is shown by the straight arrows. In the opposite direction through the same longitudinal side substances given up by the skin may enter into the breathing compensation zones, as is indicated by the arrows 24.

FIG. 5 shows a part of an active ingredient zone 4 and a part of a transmission zone 26 bearing on this on the inside. Over the whole width of these two zones an electrical voltage is so applied that the outer side of the active ingredient zone 28 is negatively poled and the inner side of the transmission zone 30 is positively poled. This voltage may for example be applied with the help of a foil battery. Negative active ingredient ions or molecules migrate as is indicated by the arrows 32 from the active ingredient zone into the transmision zone towards the positive pole 30.

What is claimed is:

1. An insert for a bra, the insert (1) shaped generally in the form of a bra cup, the insert comprising a layer having at least one zone (4) storing an active ingredient and delivering the active ingredient to the skin, the layer further having at least one active ingredient free breathing compensation zone wherein the breathing compensation zone (6) absorbs substances given up by the skin.

2. An insert according to claim 1, characterised in that the zone storing the active ingredient is at the same time a breathing zone.

3. An insert according to claim 1, characterised in that total surface of the zones (4, 6) corresponds essentially to the total surface of the insert (2).

4. An insert according to claim 1, characterised in that a multitude of active ingredient zones (4) and a multitude of compensation zones (6) are arranged alternately about the periphery of the insert.

5. An insert according to claim 1, characterised in that a multitude of zones of the one type, that is of active ingredient zones (4) or of compensation zones (6) are arranged separated from one another and the regions therebetween form the zone of the other type, i.e. a compensation zone (6) or an active ingredient zone (4).

6. An insert according to claim 1, characterised in that zones are arranged strip-shaped in the circumferential direction or the longitudinal direction.

7. An insert according to claim 6, characterised in that the zones arranged separated from one another comprise a round circumferential shape.

8. An insert according to claim 1, characterized in that the insert (2) comprises several layers of which one contains the active ingredient and compensation zone (4, 6).

9. An insert according to claim 8, characterised in that the insert (2) comprises a layer, externally bordering the layer containing the active ingredient and compensation zones (4, 6), which is breathing and at least in the regions neighbouring the active ingredient zones (4) is permeable to fluid.

10. An insert according to claim 8, characterised in that the insert (2) comprises a layer, internally bordering the active ingredient and compensation zones (4, 6), which is for transmitting the active ingredients (22) or substances to be absorbed by the compensation zones.

11. An insert according to claim 8, characterised in that the insert (2) comprises a removable protective film as an innermost layer.

12. An insert according to claim 1, characterised in that the border surfaces (20) between active ingredient zones and compensation tones (4, 6) bordering one another have a limited permeability.

13. An insert according to claim 1, characterised in that the insert (2) consists of flexible material.

14. An insert according to claim 1, characterised in that it comprises thermoplastic material at least on the inner side, which with body surface temperature adapts to the skin and ensures a good skin contact.

15. An insert according to claim 1, characterised in that the insert (2) is a rolled up flat strip with a self-adhesing closure.

16. An insert according to claim 15, characterised in that the flat strip comprises weakening lines for shortening the strip.

17. An insert according to claim 1, characterised in that the insert (2) in the longitudinal direction comprises a separating line and two lateral regions (8, 10) adjustably overlap along the line.

18. An insert according to claim 1, characterised in that the insert (2) comprises recesses (16) in the longitudinal direction.

19. An insert according to claim 1, characterised in that the insert (2) externally comprises at least a self-adhesing region for fastening to the bra.

20. An insert according to claim 1, characterised in that the active ingredient zones (4) are hygroscopic.

21. An insert according to claim 1, characterised in that it is constructed such that there exists a pressure difference between the active ingredient zones (4) and the skin.

22. An insert according to claim 1, characterised in that it is so constructed and the active ingredient is so incorporated that the active ingredient transport to the skin is effected by falls in concentration (controlled release).

23. An insert according to claim 1, characterised in that a toil battery is arranged in such a manner that an electrical voltage (28, 30) is applied over the thickness of the active ingredient zones (4).

24. An insert according to claim 1, characterised in that the active ingredient zones (4) on the inner side are limited by a diaphragm-like separating layer.

25. An insert according to claim 1, characterised in that the active ingredients (22) are located in a substance or form a substance which liquifies on heating.

26. An insert according to claim 1, characterised in that the active ingredients (22) are located in a substance or form a substance which is thixotropic.

27. An insert according to claim 1, characterised in that the active ingredient zones (4) on the inside are limited by a membrane whose permeability to the active ingredients (22) increases on heating.

28. An insert according to claim 1, characterised in that the active ingredient zones on the inside are limited by a membrane whose permeability to the active ingredients (22) increases with the effect of force by changes in movement of the insert (2).

29. An insert according to claim 1, characterised in that the active ingredient zones (4) are border surface systems with border-surface-active active ingredients (22).

30. The insert of claim 1 having a generally frustoconical shape.

31. The insert of claim 1 wherein the layer comprising the zone storing an active ingredient and the breathing zone is a skin contacting layer.

* * * * *